United States Patent [19]

Meyer

[11] 4,020,345
[45] Apr. 26, 1977

[54] DETECTOR FOR AN INFRARED ANALYZER

[75] Inventor: Emilio G. Meyer, Rozzano (Milan), Italy

[73] Assignee: Leeds & Northrup Italiana S.p.A., Milan, Italy

[22] Filed: Oct. 22, 1975

[21] Appl. No.: 624,654

[30] Foreign Application Priority Data

Oct. 22, 1974  Italy .................................. 28656/74

[52] U.S. Cl. .............................. 250/343; 250/346
[51] Int. Cl.² ........................................ G01N 21/26
[58] Field of Search ............ 250/343, 344, 345, 346

[56] References Cited
UNITED STATES PATENTS

| | | | |
|---|---|---|---|
| 3,517,189 | 6/1970 | Meyer | 250/344 |
| 3,899,252 | 8/1975 | Dimeff | 250/343 |
| 3,911,277 | 10/1975 | Cederstrand | 250/344 |

*Primary Examiner*—Craig E. Church
*Attorney, Agent, or Firm*—Diller, Brown, Ramik & Wight

[57] ABSTRACT

A detector for an IR analyzer is disclosed, wherein the blank sample (that is, a quantity of the compound which is searched in a liquid or gaseous sample in which the component is searched for) is replaced by an optical filter, preferably an interference filter. A combination of reflecting walls for the instrument casing and the inner body is also disclosed, the assembly being completed by a window for the flow of the IR radiations and by two thermistors inserted in a Wheatstone bridge circuitry, the unbalances of which are exploited both for detecting the presence of the searched for component and for measuring its concentration by comparison.

9 Claims, 6 Drawing Figures

DETECTOR FOR AN INFRARED ANALYZER

This invention relates to a detector adapted to the use in an infrared ray analyzer for detecting the presence and the concentration of a specific component in a liquid or gaseous sample.

Analyzers are known in which the presence and the concentration of a certain component of a liquid or gaseous sample are detected by having a radiant energy beam through the sample and by measuring downstream thereof the amount of infrared (IR) frequency energy which have been possibly absorbed by the compound being investigated.

In the first analyzers of this kind, the metering of the amount of energy absorbed by the component during the flow of the radiant energy through the sample being analyzed was mainly entrusted to a thermistor detector comprising a first thermistor exposed to the radiations emerging from the sample being analyzed, a second thermistor from the sample being analyzed, a second thermistor is exposed directly to the source radiation and a Wheatstone bridge including both thermistors, which was initially balanced for a zero absorption of energy between the radiant energy source and the first thermistor (that is, no example being present) and, upon the insertion of the sample to be analyzed, gave thus the measure of the amount of energy which had possibly been absorbed by the investigated component of the sample being analyzed, as a function of the resultant bridge unbalance.

To prevent possible variations of the ambient conditions and/or the composition of the sample, which had a bearing only on the thermistor exposed to the radiations flowing through the sample, from prejudicing the correct measuring of the concentration of the investigated component, there has been introduced in the most updated detectors, the idea of exposing, rather than a single thermistor, both thermistors to the radiations as caused to flow through the sample (so that possible modifications of the sample may evenly influence both thermistors) and inserting between the sample and either thermistor a predetermined quantity of the component to be investigated, so that, after an initial bridge balancing as carried out without inserting any sample, the insertion of the sample to be analyzed between the radiation source and the detector does not originate any substantial variations in the response of the above mentioned thermistor (which thus becomes a reference thermistor) while causing, conversely, in the other thermistor (or detecting thermistor) such a response variation as to give to rise a bridge unbalance the magnitude of which is proportional to the quantity of radiant energy which had been absorbed by the searched component as the radiation is caused to flow through the sample, and thus also to the concentration of the same component in the sample being analyzed.

The detectors of the latter type, that is those having both thermistors exposed to the radiations emerging from the sample being analyzed, are doubtless preferred to the former types, inasmuch as the degree of accuracy of the readings taken is nowise influenced by variations of ambient conditions and/or of components of the sample, which act to the same degree on both thermistors. Regrettably, there are other, not negligible difficulties which are bound to the presence of the reference component, such as the necessity of providing, in the detector, a reliably sealtight housing for the component itself and the requirement of having always available a component in conditions of absolute purity. It is to be recalled, moreover, that the properties of the component inevitably vary with the lapse of time.

In the light of the foregoing considerations, it is an object of the present invention to provide a detector for an IR-analyzer which is capable of carrying out the measure of the quantity of radiant energy as absorbed by a determined component contained in a sample on which radiant energy is caused to impinge, and thus the measure of the concentration of same component in the sample being analyzed, by exploiting the above referred to principle of comparing the responses of two thermistors, both exposed to the radiations emerging from the sample, but without requiring the use of a predetermined quantity of the component as properly contained in the detector in a position which is intermediate between the sample and either thermistor.

According to the invention, this object is achieved by a detector which is characterized in that it comprises an outer casing having its inner walls of a reflecting nature, a transparent window formed through said casing to allow the flow of the radiation beam emerging from the sample being analyzed, an inner body having its outer walls reflecting placed in the interior of said casing, a first chamber formed in said inner body with an inlet confronting said window, a second chamber formed through said inner body with an inlet which is not confronting said window, an optical filter arranged at the inlet of said first chamber to have only a restricted band of frequencies lying in the IR-frequency field absorbed by the component being searched and two thermistors which are housed in each of said chambers, respectively, and electrically inserted in a bridge circuit capable of being balanced and equipped with an unbalance-measuring instrument.

Thus, the detector according to the invention is based on the already known principle of exposing both thermistors to the radiation emerging from the sample being analyzed, while concurrently providing for inserting between the sample and either thermistor an optical filter (preferably of the interference type) which, in combination with the different locations of the inlets of the two thermistor-housing chambers relative to the radiation inlet window, acts in such a way that, the fraction of the radiation beam entering the detector which lies in the frequency band of the filter, may affect for the predominant portion the filter-shielded thermistor, whereas the remaining fraction, more particularly the one which is outside the aforesaid frequency band, goes to affect the other thermistor after several reflexions as brought about by the reflecting walls of the outer casing and the inner body. It is thus apparent that the possible absorption of a certain amount of radiant energy by the component which is being searched in a sample positioned between a radiant energy source and the detector according to the invention has but a negligible effect on the thermistor which is not shielded by the filter, while reducing the quantity of energy impinging on the filter-shielded thermistor to such a degree as to vary the resistive value thereof considerably. Obviously, the result is a considerable bridge unbalance, the magnitude of which is a measure of the quantity of energy absorbed by the compound being searched in the analyzed sample and thus of the concentration of such component in the sample.

It can easily be understood that the most prominent difference between the detector according to the invention and the conventional detector of the same class (that is, with both thermistors exposed to the radiations emerging from the sample being analyzed) lies in that the shielding member which is used for either thermistor is not the same component which is being searched, but an optical filter. This fact means that the detector according to the invention, while retaining the advantages of the conventional detectors as regards the constancy of the degree of accuracy of the readings as the ambient conditions and the composition of the sample are viewed, is exempt, on the other hand, from those problems of sealthightness, purity and aging which arise in the conventional detectors as a result of the use of a quantity of the searched compound as the shielding member.

The foregoing and other features of the present invention, along with the advantages stemming therefrom, will become apparent from the scrutiny of the ensuing detailed description of a preferred embodiment thereof as shown by way of example in the accompanying drawings, wherein.

Figures 1, 2:
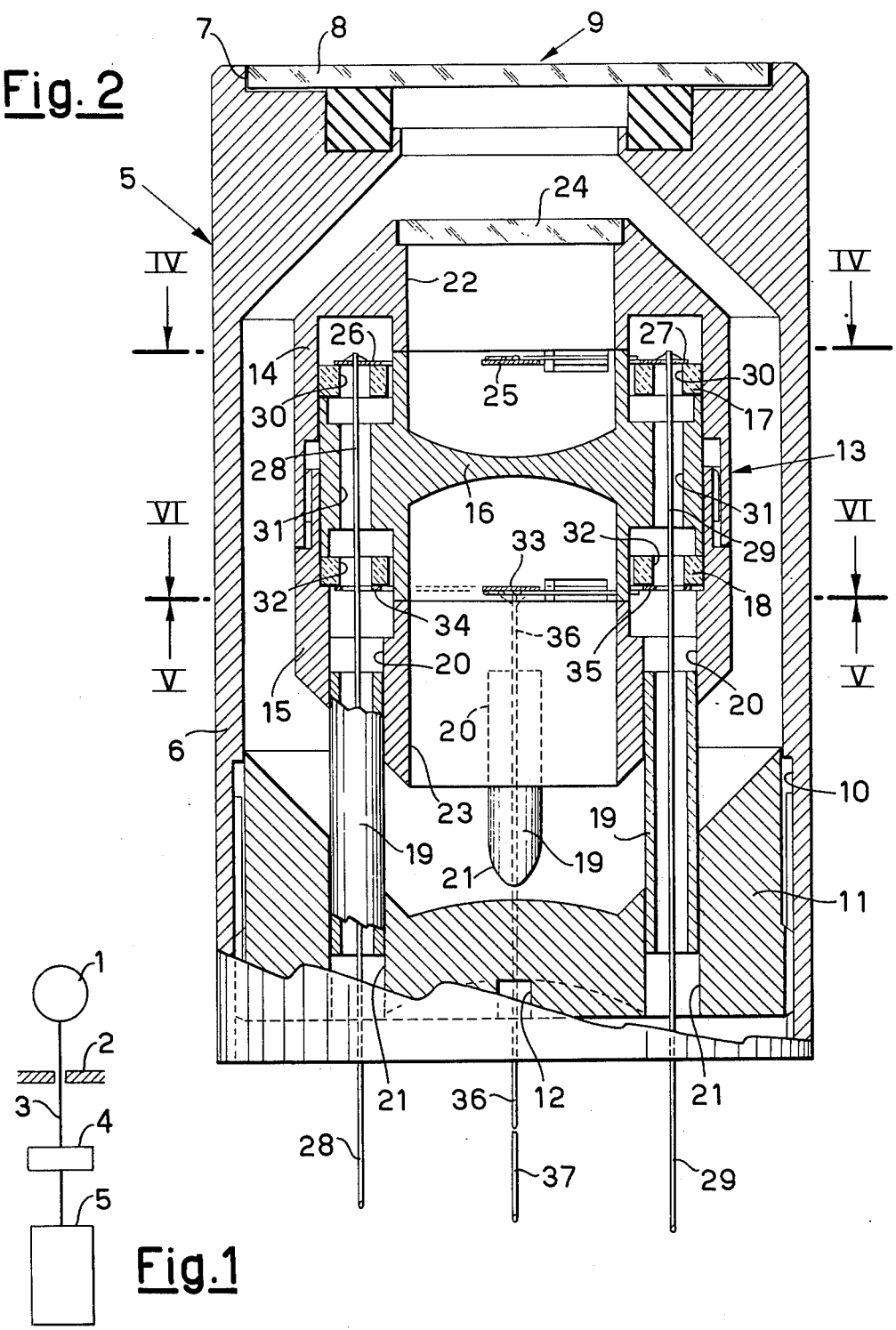
FIG. 1 shows the principle diagram of an IR-analyzer in which the detector according to the invention can be used.
FIG. 2 shows the mechanical parts, in axial cross-sectional view taken along the line II—II of FIG. 4, of a preferred embodiment of the detector according to the invention.

The detector as shown in the drawings, and, in general the detector according to this invention, is considered as being intended to be an integral part of an IR-analyzer of the kind as diagrammatically shown in FIG. 1.

Such an analyzer comprises a source of radiant energy 1 which, with the aid of a collimating member 2, is adapted to direct a radiation beam 3 against a liquid or gaseous sample 4, in which it is desired to detect both the presence and the concentration of a specific component. The radiation beam emerging from the sample 4, where it has undergone a certain absorption of energy which, for the searched component lies within a restricted field of IR-frequencies, is collected by a detector 5 which is capable of measuring the quantity of energy which has been absorbed by the component concerned and gives, in relation with such a quantity, the measure of the concentration of the component in the sample being analyzed.

Figure 3:
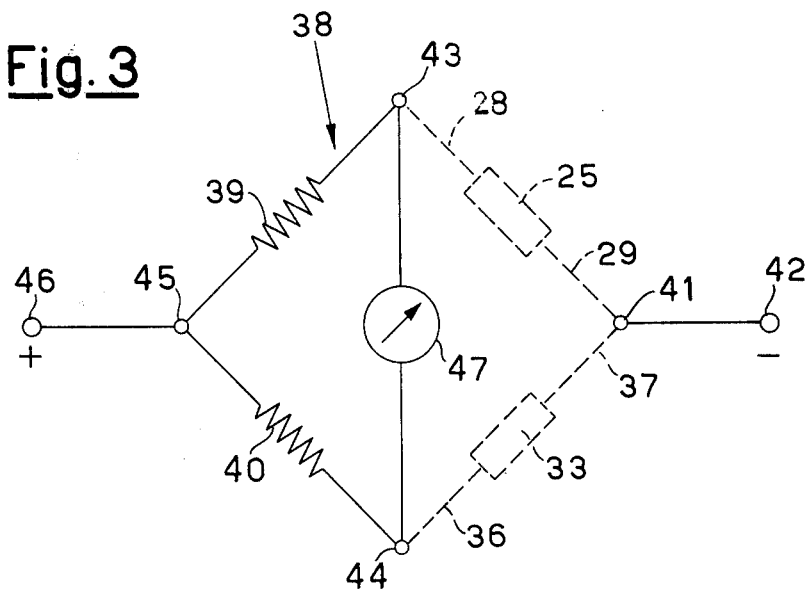
FIG. 3 shows the diagram of a bridge electric circuitry which completed the detector as shown in FIG. 2.

According to the invention, it is provided to use as the detector 5, just a novel and improved detector, an example of which is shown in FIGS. 2 to 6. This detector can be regarded as being composed by a part which is more properly mechanical, as depicted in FIGS. 2, 4, 5 and 6, and a part which is more properly electrical, as shown in FIG. 3.

Figure 6:
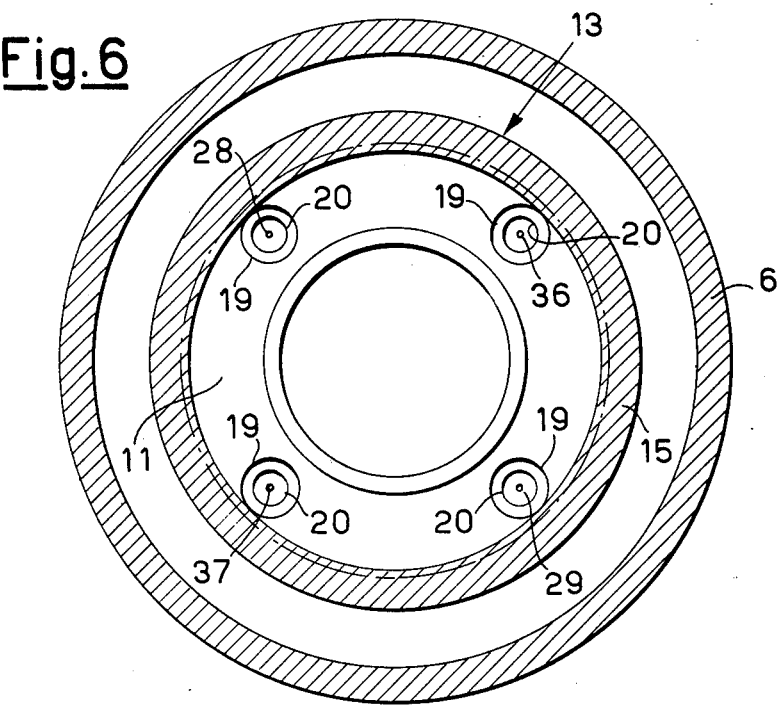
FIG. 6 shows the detector in cross-sectional view taken along the line VI—VI of FIG. 2.
Figure 4:
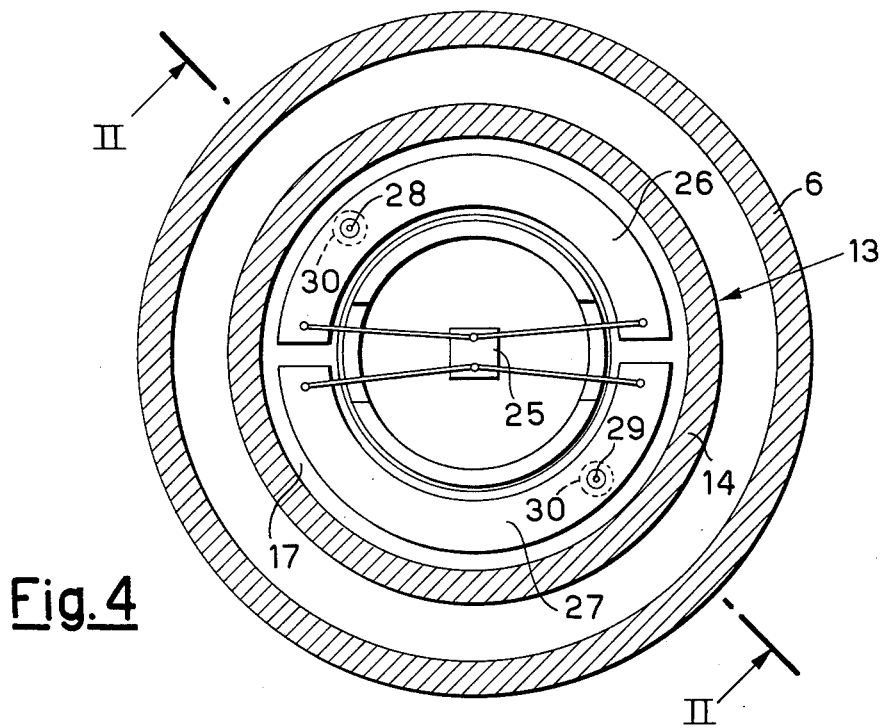
FIG. 4 shows the detector in cross-sectional view taken along the line IV—IV of FIG. 2.

The mechanical part as shown in FIGS. 2, 4 and 6 comprises an outer casing 6 having glossy inner walls (and thus they reflect the radiations impinging thereon), which is provided with a top opening 7 fitted with a shielding glass 8 forming a transparent window 9 adapted to permit the flow of a radiation beam 3 emerging from the sample being analyzed, and with a bottom port 10 closed by a screwable stopper 11 having a screwdriver slot 12.

Within the cylindrical inner cavity of the casing 6 a body 13, also cylindrical, is arranged, the outer walls of which are glossy (and thus radiation-reflecting). As can be seen in FIG. 2, the inner body 13 is substantially composed by two end annular pieces 14 and 15 which are superposed and screwably affixed to one another, an annular intermediate piece 16 and two ceramic rings 17 and 18 superposedly arranged beneath the intermediate piece 16, the body 13 being made integral with the stopper 11 by four cylindrical tubular uprights 20 and 21, the latter being forcibly inserted in bores 20 of the lower piece 15 of the inner body 13 and in bores 21 of the lower closure stopper 11, respectively.

The three cooperating pieces 14, 15 and 16 are so shaped as to define for the inner body 13 two superposed chambers 22 and 23 (FIG. 2), the first of which has its inlet confronting the transparent window 9 and shielded by an optical interference filter 24 which is adapted to allow the flow of those radiations only which are comprised in a narrow frequency band in the IR-frequency field of radiation capable of being absorbed by the searched component in the sample being analyzed, and the second has its inlet pointing towards the opposite side and devoid of any protection.

In the interior of the shielded top chamber 22 there is housed a thermistor 25, which is supported by the ceramic ring 17 and is electrically connected to two half-ring conductive sectors 26 and 27 formed on the top surface of the ceramic ring 17 (FIG. 4). From the conductive sectors 26 and 27 start the respective conductive wires 28 and 29 (FIG. 2), which are welded at their tops to the conductive sectors and emerge at their lower ends from the inner body 13 and then from the outer casing 6 and run through two holes 30 formed through the ceramic ring 17, two holes 31 through the intermediate piece 16, two holes 32 through the ceramic ring 18, two holes 20 through the bottom piece 15, the internal hollow spaces of the tubular uprights 19 and two holes 21 through the closure stopper 11.

Figure 5:
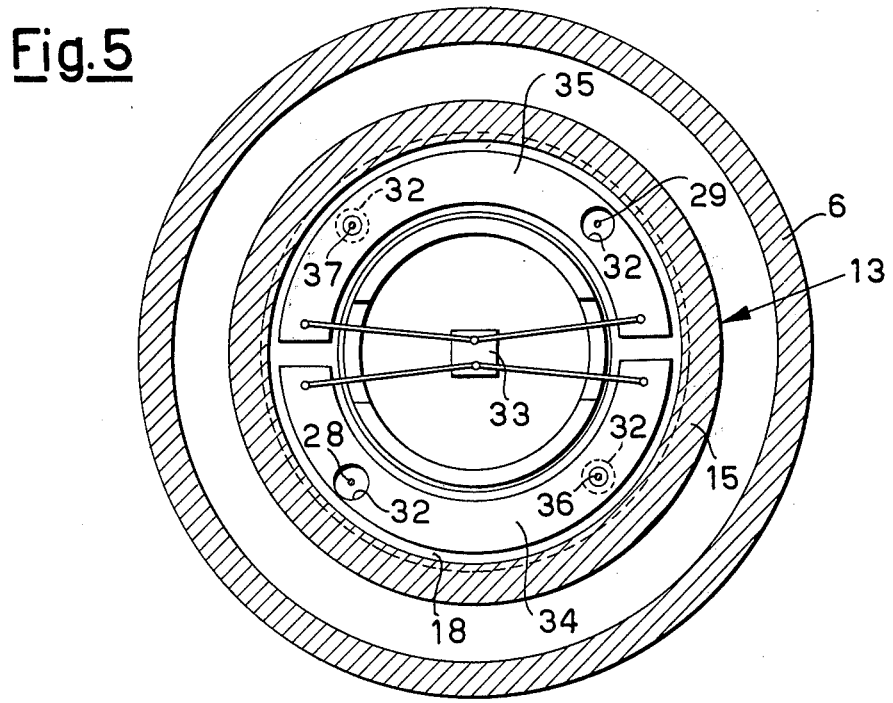
FIG. 5 shows the detector in cross-sectional view taken along the line V—V of FIG. 2.

In the interior of the upper unshielded space 23 there is housed, in its turn, another thermistor 33, which is supported by the ceramic ring 18 and is electrically connected to two half-ring conductive sectors 34 and 35 as formed on the top surface of said ceramic ring 18 (FIG. 5). From the conductive sectors 34 and 35 start the respective conductive wires 36 and 37 (FIG. 2) which are welded at their tops to the same conductive sectors 34 and 35 and emerge at their bottoms from the inner body 13 and then from the outer casing 6 by being passed through two additional holes 32 through the ceramic ring 18, two additional holes 20 through the bottom piece 15, two additional tubular uprights 19 and finally through two additional holes 21 through the closure stopper 11.

As a result, from the casing 6 of the mechanical portion of the detector of FIGS. 2 to 6 there emerge four conductive wires 28, 29 and 36, 37, the first two of which are the connection leads of the thermistor 25 and the second two are the connection leads of the thermistor 33. These conductors actually serve electrically to insert the two thermistors 25 and 33 in a Wheatstone bridge circuit 38 (FIG. 3), which constitutes the electrical part of the detector of FIGS. 2 to 6 and comprises, in addition to the thermistors aforementioned, two electric resistors 39 and 40. More exactly, the two conductors 29 and 37 connect the two thermistors 25 and 33 to a common node 41 which is connected to a negative feed terminal 42, whereas the two conductors 28 and 36 connect the same thermistors 25 and 33 to respective nodes 43 and 44 which are connected by the resistors 39 and 40 to a common node 45, the latter being connected, in turn, to a positive feed terminal 46. Between the two nodes 43 and 44 there is connected, lastly, a measuring instrument 47 (for example a galvanometer) which is adapted to sense and measure the unbalances of the bridge 38.

The operative principle of the detector shown in FIGS. 2 to 6 is as follows. A portion of the radiation which enters the detector through the transparent window 9, penetrates the upper chamber 22 and influences the thermistor 25 whereas the remaining portion after several reflections brought about by the reflecting walls of the outer casing 6 and the inner body 13, enters the lower chamber 23 and influences the thermistor 33. The presence of the interference filter 24 at the inlet of the upper chamber 22 and the position of the inlet of the chamber 22 confronting and near to the transparent window 9 act in such a way that the radiations which influence the thermistor 25 comprise only the frequencies lying within the pass band of the filter 24 and, on the other hand, the predominant majority of such frequencies go to influence the thermistor 25 rather than the farther thermistor 33. In addition, the particular conformation of the inner walls of the casing 6 and the outer walls of the body 13 (that is, summing up, the particular conformation of the space as confined between the casing 6 and the inner body 13 act in such a way that the percentage ratio between the portion of such frequencies which goes to influence the thermistor 25 and that which goes to influence the thermistor 33 can be varied by axially shifting the inner body 13 (by either screwing or unscrewing the stopper 11) so as to vary the cross-sectional area of the communication path between the window 9 and the inlet to the lower chamber 23.

By exploiting this operative principle the detector of FIGS. 2 to 6 is thus intended for being operated as follows. A preliminary calibration step is carried out at the outset, to be effected by exposing the transparent window 9 of the detector directly to the radiation beam as emitted by the source 1 as such (the sample to be analyzed, thus, is not yet inserted between the source of radiant energy and the detector) and by screwing or unscrewing the closure stopper 11 until such time as the obtention of an apropriate percentage ratio between the quantity of radiations impinging on both the thermistors 25 and 33 enables the measuring instrument 47 to signal the accurate balance of the bridge 38.

On completion of this operation, the sample to be analyzed is inserted between the radiation source and the detector, that is, the detector is exposed to the radiation beam now emerging from the sample in which the presence of the component concerned is searched in order subsequently to measure its concentration. If the sample being analyzed does not contain the searched component the status of the thermistor 25 does not vary inasmuch as no energy absorption takes place at the frequencies lying within the pass-band of the filter 24; conversely, while to a small degree, the status of the thermistor 33 is varied (a small energy absorption takes place anyhow in the sample being analyzed) so that the bridge 38 is slightly unbalanced in a certain direction. If, conversely, the sample contains the searched component, the energy absorption produced thereby has still a slight influence on the state of the lower thermistor 33, but it concurrently has a considerably stronger influence on the thermistor which up to that time received the predominant fraction of the frequencies that it now absorbs, that is, on the upper thermistor 25. This fact originates a strong unbalance of the bridge 38 in a direction opposite to the previous one, and this unbalance is measured by the measuring instrument 47: the indications of the latter, for it being a measure of the quantity of energy absorbed by the searched component, also gives the expected measure of the concentration of such component in the sample being analyzed.

To the detector as described above there can be made modifications and changes within the scope of the invention as claimed herein. One of these changes, more particularly, can be the arrangement, at the inlet to the lower chamber 23, of an additional optical interference filter capable of selecting only a portion of the energy entering the detector. By so doing, the reference term will not be the entire energy emerging from the sample but rather a portion thereof only as allowed to pass through the additional filter.

What is claimed is:

1. A detector for use in an IR-ray analyzer of the type particularly adapted for detecting the presence and the concentration of a specific component in a liquid or gaseous sample and wherein the analyzer includes a source of radiant energy adapted to direct a radiations beam onto a sample to be analyzed and a detector for collecting radiations beam downstream of a sample and for supplying a measure of the concentration of a component which is searched for in the sample undergoing the analysis as a function of the IR-frequemcy quantity absorbed by a component during the flow of the radiations beam through a sample, said detector comprising an outer casing having reflecting inner walls, a transparent window formed in said casing for the flow of a radiations beam emerging from a sample being analyzed, an inner body having reflecting outer walls and positioned within said casing, said inner body defining a first chamber having an inlet confronting said window, said inner body also defining a second chamber having an inlet not confronting said window, an optical filter arranged at the inlet of said first chamber to allow the flow of a radiations beam of a restricted frequency band only lying in the field of the IR-frequencies which can be absorbed by a searched for component, first and second thermistors housed in said first and second chambers, respectively, said first thermistor being positioned for receiving only a radiations beam of said restricted frequency band and said second thermistor being positioned for receiving at the same time a radiations beam unaffected by said filter, and means for electrically connecting said thermistors electrically in separate legs of a bridge circuit which can be balanced and is equipped with an unbalance-measuring instrument.

2. A detector according to claim 1, characterized in that the optical filter is an interference filter.

3. A detector according to claim 1, characterized in that means mount said inner body for displacement within said casing for movement towards and away from said transparent window to vary the distance between the inlet to said first chamber and said transparent window, the inner walls of said casing and the outer walls of said inner body being so shaped that displacements of said inner body are accompanied by a variation of the cross-sectional area of a communication pathway between said transparent window and the inlet to said second chamber.

4. A detector according to claim 3, characterized in that the second chamber has its inlet pointing away of the inlet of the first chamber.

5. A detector according to claim 1 wherein the inlet to said second chamber always faces away from said transparent window, and walls of said outer casing and said inner body form means for reflecting a radiations beam passing through said transparent window into the inlet of said second chamber.

6. A detector according to claim 1 wherein the inlet to said second chamber is transparent to at least one portion of a radiations beam entering said outer casing.

7. A detector according to claim 1 wherein said first and second chambers are in axial alignment with each other and said transparent window and said inlets of said first and second chambers face in opposite directions.

8. A detector according to claim 1 wherein the inlet to said second chamber always faces away from said transparent window, said inner body blocks direct entry of a radiations beam passing through said transparent window into the inlet of said second chamber, walls of said outer casing and said inner body define a restricted passage for a radiations beam to the inlet of said second chamber, and means mount said inner body for movement relative to said outer casing to selectively vary the cross-section of said restricted passage.

9. A detector according to claim 8 wherein the direction of movement of said inner body is generally towards and away from said transparent window.

* * * * *